(12) United States Patent
Rebentisch et al.

(10) Patent No.: US 9,233,239 B2
(45) Date of Patent: Jan. 12, 2016

(54) SPRING CONTACT COMPONENT, PLUG CONTACT SOCKET, AND CONTACT SOCKET COMPONENT

(71) Applicant: BIOTRONIK SE & Co. KG, Berlin (DE)

(72) Inventors: Ronald Rebentisch, Berlin (DE); Stefan Lehmann, Wriezen (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 14/299,666

(22) Filed: Jun. 9, 2014

(65) Prior Publication Data

US 2015/0018909 A1    Jan. 15, 2015

Related U.S. Application Data

(60) Provisional application No. 61/844,862, filed on Jul. 11, 2013.

(51) Int. Cl.

| H01R 13/33 | (2006.01) |
| A61N 1/05 | (2006.01) |
| H01R 13/187 | (2006.01) |
| A61N 1/36 | (2006.01) |
| H01R 13/17 | (2006.01) |
| H01R 43/16 | (2006.01) |

(52) U.S. Cl.
CPC .. *A61N 1/05* (2013.01); *A61N 1/36* (2013.01); *H01R 13/17* (2013.01); *H01R 13/187* (2013.01); *H01R 43/16* (2013.01); *H01R 2201/12* (2013.01); *Y10T 29/49195* (2015.01)

(58) Field of Classification Search
CPC ......................... H01R 13/187; H01R 2201/12
USPC .......................................... 439/840, 841, 909
See application file for complete search history.

(56) References Cited

U.S. PATENT DOCUMENTS

| 6,895,276 B2 * | 5/2005 | Kast et al. ..................... 439/909 |
| 7,274,964 B2 * | 9/2007 | Balsells ........................ 439/909 |
| 8,428,724 B2 * | 4/2013 | Sage ............................. 439/909 |
| 8,934,974 B2 * | 1/2015 | Sage ............................. 439/909 |

FOREIGN PATENT DOCUMENTS

| JP | 2002217046 | 8/2002 |
| JP | 2010147199 | 7/2010 |
| JP | 2011023561 | 2/2011 |
| WO | 2006026186 | 3/2006 |

OTHER PUBLICATIONS

European Search Report and Notes to the European Search Report on European Patent Application No. EP 14 17 2272, dated Dec. 16, 2014 (5 pages).

* cited by examiner

*Primary Examiner* — Tho D Ta
(74) *Attorney, Agent, or Firm* — Buchanan Ingersoll & Rooney PC

(57) ABSTRACT

A spring contact component for a plug socket of an electromedical implant, with a coil surrounding the outer periphery of a plug opening. A simpler, more cost effective and automatable design of a plug socket module can be achieved in that at least one end of the coil is electrically and mechanically connected directly to a connector pin via a wire-shaped and/or strip-shaped element. The invention also relates to a corresponding plug socket module, a modular header, and a method for producing a spring contact component of this type.

15 Claims, 5 Drawing Sheets

SPRING CONTACT COMPONENT, PLUG CONTACT SOCKET, AND CONTACT SOCKET COMPONENT

CROSS-REFERENCE TO RELATED APPLICATIONS

This patent application claims the benefit of U.S. Provisional Patent Application No. 61/844,862, filed on Jul. 11, 2013, the disclosure of which is hereby incorporated by reference in its entirety.

TECHNICAL FIELD

The present invention relates to a spring contact component for a plug contact socket of an electromedical implant with a coil surrounding the outer periphery of a plug opening, said coil having a first (coil) end and a second (coil) end, and also to a method for producing said spring contact component, to a corresponding contact socket component, a corresponding plug contact socket, and a corresponding electromedical implant.

BACKGROUND

A wide range of medical implants are known from the prior art. In conjunction with the present invention, an electromedical implant is understood to be an active implant, which, besides a power supply (for example, a battery), also comprises further electrical and/or electronic components (for example, capacitors), which are arranged in a housing that is hermetically sealed. Electromedical implants of this type include, for example, cardiac pacemakers, defibrillators or neurostimulators. These implants are used to excite the biological tissue by means of electrical pulses, which are generated by a pulse generator provided in the housing.

Implants of this type are often connected to electrode lines, which, after implantation in a body, are used to treat said body, for example, to transmit and/or deliver stimulation pulses and/or defibrillator shocks to specific points of the body, or are used to detect electric potentials of points of the body. To this end, an electrical connection has to be produced between the electrical and/or electronic components arranged inside the housing and the electrode line. This electrical connection is generally produced by means of a bushing, and what is known as a terminal housing. Here, a bushing ensures an electrical connection between the interior of the housing and the external environment, and is responsible at the same time for the hermetic seal of the housing. The terminal housing fastened via the bushing further guides the electrical connection of the bushing to a contact point, which is often formed as a plug contact socket. The connector piece (e.g., plug) of the electrode line is introduced after implantation into the generally standardized plug contact socket. Electrical contact is thus produced at the contact points of the plug contact socket between the electronic components of the implant, for example, a pulse generator, and the contact points of the connector piece of the electrode line and, therefore, of the electrode fastened thereto.

The interface between the implant and the electrode line is normally designed as a detachable multipoint connection and is defined in terms of its geometry via ISO standards. A coaxially stepped, double pug connection with sealing lips is defined in Standard ISO 5841-3 (IS-1 Standard) for pulse generators with cardiac pacemaker function, that is to say for pulse generators that operate with low-voltage pulses. A coaxially stepped, quadruple plug connection (of which three are in-line and smooth) with sealing lip systems integrated in the socket opening is defined in Standard ISO 27186 (DF4/IS4 Standard) for pulse generators with cardiac pacemaker function and/or defibrillator function, that is to say with high-voltage and low-voltage pulses. By contrast, there are no standard guidelines for a plug/socket geometry of neurostimulators. In products known at the time of filing of the present application, plug/socket systems with eight coaxial-smooth plug connections with sealing lip systems integrated into the socket opening are used, for example.

In the mentioned plug systems, all contactings can be formed in principle via spring contacts, provided specific demands in terms of the plug-in force, retention force and pull-out force, and also the electrical contact stability, are met.

In the known plug contact sockets, the sealing lip systems in life-sustaining implants (cardiac pacemakers, defibrillators, etc.) are normally designed redundantly, that is to say sealing lip pairs are used on either side of the individual electrical contact regions in order to keep bodily fluid away from the contact point, and also to electrically insulate the contact points from one another. In the case of implants that are not life-sustaining (for example, neurostimulators), a deviation is made from this rule.

From document International Publication No. WO 2006/026186, an implant with a plug contact socket for a multipoint plug connection is known, which has a plurality of electrically conductive, toroidal contact springs (spring coils). Here, each spring coil is arranged in a corresponding metal spring ring in such a way that the spring coil surrounds the outer periphery of the opening for the introduction of the plug at the respective point. Furthermore, on each spring ring, a wire feed line fastened thereto is provided and produces the electrical contact with the interior of the implant housing. The unit formed from a spring coil, the associated spring ring and the wire feed line fastened thereto is also referred to as a spring contact component. Together with the plastic housing likewise disclosed in the above document, a contact socket component is formed.

In other known solutions, the spring ring is omitted and the toroidal contact spring is mounted in a spring cage made of electrically conductive material. Here, the spring cage is often produced as a metal form-milled part. The contact socket component is assembled manually from the spring coil and spring cage. In a further manual method step, plug contact sockets are produced by stringing together contact socket components and sealing socket components alternately. Automated production of plug contact sockets is not possible due to design constraints. The known solution is additionally overstressed with consideration of the process-induced shape and position tolerance of its individual components and, therefore, non-uniform forces may act on a real electrode plug fitted into such a plug contact socket and could consequently lead to malfunctions. It has also proven to be disadvantageous with such a known solution that the occupied installation space is comparatively bulky and does not allow any further volume reduction. The seal between the modularly constructed metal-conductive contact socket components and the intermediate electrically insulating sealing socket components additionally appears to be problematic.

An object is therefore to create a plug contact socket for a terminal housing that avoids the above disadvantages and, in particular, can be produced in a simple manner in terms of the equipment involved and, therefore, cost effectively. The plug contact socket should also conform to the above-specified standards.

The present invention is directed toward overcoming one or more of the above-identified problems.

SUMMARY

At least the above object is achieved by a plug contact socket according to claim 8 comprising a novel spring contact component having the features in claims 1 and 2.

In accordance with the present invention, and as shown in FIG. 1, the second end (5.2) of the coil (5) and the wire-shaped and/or strip-shaped element (10), as well as a connector pin (12), are formed in one piece. Alternatively, in accordance with the present invention, at least the second end of the coil of the spring contact component surrounding the plug opening is likewise connected electrically and mechanically via a wire-shaped and/or strip-shaped element directly to a connector pin. The connector pin is used here for electrical connection of the spring contact component to the electrical/electronic components arranged in the housing interior of the implant via the header and the bushing of the implant. In both alternative solutions, the housing of the contact socket component can consist of the same material or the same material group (for example, non-conductive polymers) as the sealing socket components. The housing of the contact socket component may also be fabricated from an electrically insulating material in the form of a cost-effective injection molded part. The electrically insulating material can be selected such that the different socket components can be glued together. A possible infiltration of liquid into the electrical contact region is thus advantageously prevented.

The definition that a wire-shaped and/or strip-shaped element constitutes the direct connection to the connector pin implies that further bulky elements are not present between the connector pin and the coil.

In a preferred exemplary embodiment, the first end of the coil forms a connector pin.

The merit of the inventors herein lies in having found a simpler design of the spring contact component, in which the connector pin is integrated into the coil or in which the connector pin is electrically or mechanically connected to the coil merely via a wire-shaped and/or strip-shaped element. It is thus possible to dispense with further electrical feed line components, which further simplifies the production. The simpler design of the spring contact component leads to lower costs during the production process, which can now be automated. With the spring contact components according to the present invention, modular plug sockets can be fabricated that conform to the above-specified standards.

In a preferred exemplary embodiment, the wire-shaped and/or strip-shaped element has a dimensionally stabilizing means surrounding the coil outwardly in the region of the periphery of said coil. In this preferred exemplary embodiment, the conventional metal housing (spring cage), that would have previously received the coil and was formed as a form-milled part, can be omitted in accordance with the present invention. In a preferred embodiment of the present invention, the dimensionally stabilizing means is formed as a single or multiple ring or as a spiral, which preferably bears against and surrounds the outer periphery of the coil arranged within the single or multiple ring. A single or multiple ring of this type is placed outwardly around the coil to a certain extent in the region of the periphery of the coil, and thus has a dimensionally stabilizing effect.

It is also advantageous if the dimensionally stabilizing means is connected at a number of points to the coil, for example, via laser welding spot welds or by electrically conductive self-curing plastics or adhesives.

The spring contact component is preferably fabricated form electrically conductive material, for example, from spring-tempered implant alloys, from a platinum-iridium alloy, particularly preferably from Pt80Ir20. Further cost savings are produced if the wire-shaped and/or strip-shaped element and the coil of the alternative solution are fabricated from the same, electrically conductive material. The electrical voltage, for example, a voltage pulse, is then conducted from the interior of the implant housing, via the bushing and the header, the connector pin, the wire-shaped and/or strip-shaped element and the coil, to the plug.

In a preferred embodiment of the contact socket component according to the present invention, the spring contact component is inserted or embedded in a housing made of an electrically non-conductive material, preferably a housing fabricated by means of injection molding, wherein the first connector pin and the second connector pin preferably protrude from the housing in the region of the outer periphery of the housing. The spring contact component is inserted there with its outwardly peripheral dimensionally stabilizing means. A contact socket component of this type can be easily produced, wherein the injection molded part preferably consists of an elastomer, and particularly preferably contains silicone. With this solution according to the present invention, a cost-intensive form-milled part is replaced by a cost-effective injection molded part, which can additionally be formed so as to be smaller since the wire-shaped and/or strip-shaped element already performs the essential dimensionally stabilizing function. Since the metal form-milled parts are often fabricated from the material MP35N, the risk of long-term contact instabilities is additionally reduced as a result of their omission.

The housing can be formed, for example, as a cylinder portion with a central, continuous opening, which has a notch in the region of the inner wall of the opening in order to receive the spring contact component. Furthermore, at least one substantially radially running continuous opening can be provided in the housing and extends in a particularly preferred embodiment as far as the notch for the spring contact component. The first and second ends of the coil, for example, which are both formed as a connector pin, are arranged in the radially running opening. Once the spring contact component has been inserted or embedded in the housing, in particular, in the notch provided on the inner wall, the radially running opening around the protruding connector pin(s) is sealed, for example, using a silicone adhesive. An improved seal of the electrically conductive component is thus achieved, and also constitutes a seal with respect to the bodily fluid. Furthermore, the required installation space for the contact socket component is restricted to a minimum, or at least lessened.

At least the above object is also achieved by a terminal housing for an electromedical implant, said housing having at least two contact socket components of the above-described type arranged side by side. This terminal housing, also referred to as a "header", can also be formed in a number of parts (e.g., in a modular manner).

The above-described at least two contact socket components are separated by an intermediately arranged sealing socket component, which can be formed as an electrically insulating injection molded part, for example, using silicone. A sealing socket component of this type is preferably formed as a circular-cylinder portion with a central continuous opening, wherein at least one sealing lip, particularly preferably a sealing lip pair, is arranged in the region of the inner wall of the continuous opening.

With both alternative solutions, the housing of the contact socket component can consist of the same material or the same material group (for example, non-conductive polymers) as the sealing socket components. The housing of the contact socket module can therefore also be fabricated from an electrically insulating material in the form of a cost-effective injection molded part. The electrically conductive material can be selected such that the different socket components can be glued together. A possible infiltration of liquid into the electrical contact region is thus advantageously prevented.

The plug contact socket of the header according to the present invention may also have more than two contact socket components. It is advantageous if adjacent contact socket components are each separated by a sealing socket component arranged there between, and if a sealing socket component is additionally provided at the open end of the plug contact socket for sealing purposes. Due to this modular design, any plug socket configurations can be produced at the header.

The method according to the present invention, solving at least one of the described, stated objectives, for producing a spring contact component for a plug contact socket of an electromedical implant with a coil surrounding the outer periphery of a plug opening comprises the following steps:

Producing a first coil and a second coil from a wire or a strip, wherein the first coil has a smaller diameter than the second coil, Forming an open torus from the first coil having the smaller diameter, Connecting, where appropriate, the first coil and the second coil together at one end of each coil, and Screwing the first coil in the form of an open torus into the second coil in such a way that the second coil forms a single or multiple ring(s) outwardly surrounding the first coil in the region of the periphery of said first coil.

Should the first coil and the second coil be fabricated from the outset from a single wire or strip, which is advantageous, the method step in which the first coil and the second soil are interconnected is omitted.

In a preferred exemplary embodiment of the method according to the present invention, the first coil is canted before the formation of the torus, whereby the spring properties of the first coil are influenced.

In order to produce an improved connection between the ring and coil, the ring in a further embodiment can be fastened, once screwed in, to a number of points of the first coil, for example, by means of laser welding or by electrically conductive self-curing plastics or adhesives.

The design and the composition of an exemplary embodiment of a spring contact component according to the present invention and of a plug contact socket of a header according to the present invention will be explained hereinafter on the basis of the Figures. Furthermore, the production method according to the present invention for producing a spring contact component according to the present invention will be explained on the basis of Figures. Here, all features illustrated and/or described form the subject of the present invention, even independently of their summary in the claims or the back-references of the claims.

Further features, aspects, objects, advantages, and possible applications of the present invention will become apparent from a study of the exemplary embodiments and examples described below, in combination with the Figures, and the appended claims.

DETAILED DESCRIPTION

Figure 1:
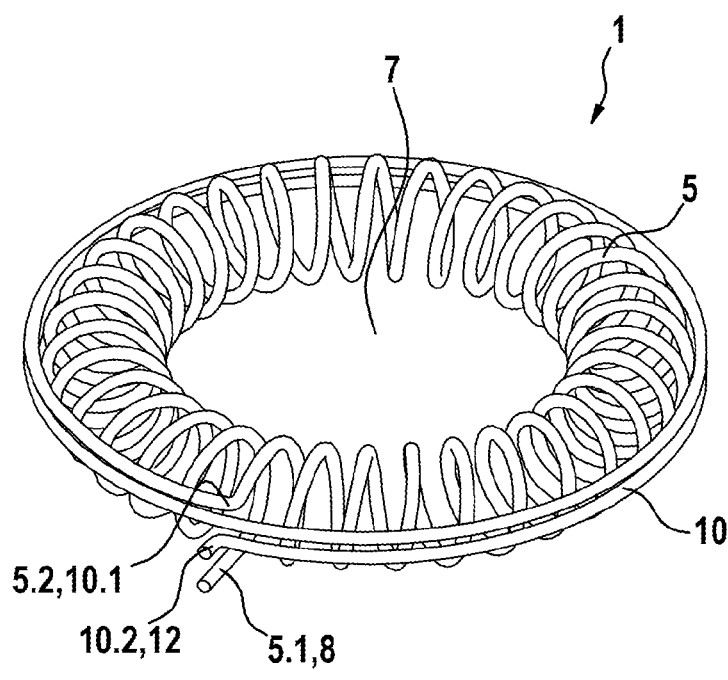
FIGS. 1-3 show three perspective views from the side of an exemplary embodiment of a spring contact component according to the present invention in the form of a toroidal contact spring.

A spring contact component in the form of a toroidal contact spring will be described hereinafter as an exemplary embodiment. The toroidal contact spring 1 according to the present invention, illustrated in FIGS. 1-3 for a plug contact socket of an electromedical implant, has an annular or toroidal coil 5, which forms centrally a continuous contacting opening 7. The plug or the connector piece of the electrode line can be plugged into said contacting opening 7 when the contact spring 1 is arranged in a plug contact socket.

The toroidal coil 5 preferably consists of a Pt80Ir20 wire having any cross-section, but particularly preferably a circular, elliptical or rectangular cross-section. The coil 5 surrounds the outer periphery of the circular or elliptical continuous plug opening 7 completely. The first end 5.1 of the coil 5 forms a first connector pin 8. The second end of the coil 5.2 transitions seamlessly into the ring 10 and ends in the connector pin 12. In other words, the coil 5, the ring 10 as a dimensionally stabilizing wire-shaped and/or strip-shaped element, and also the connector pin 12, are formed in one piece.

Figure 2:
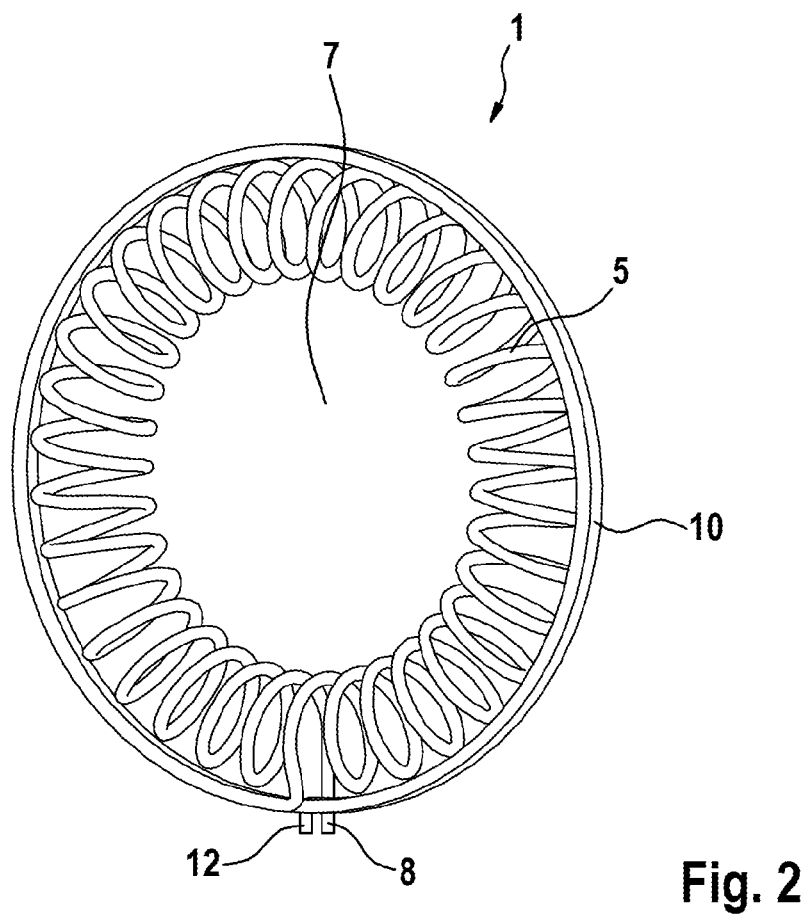
Figure 3:
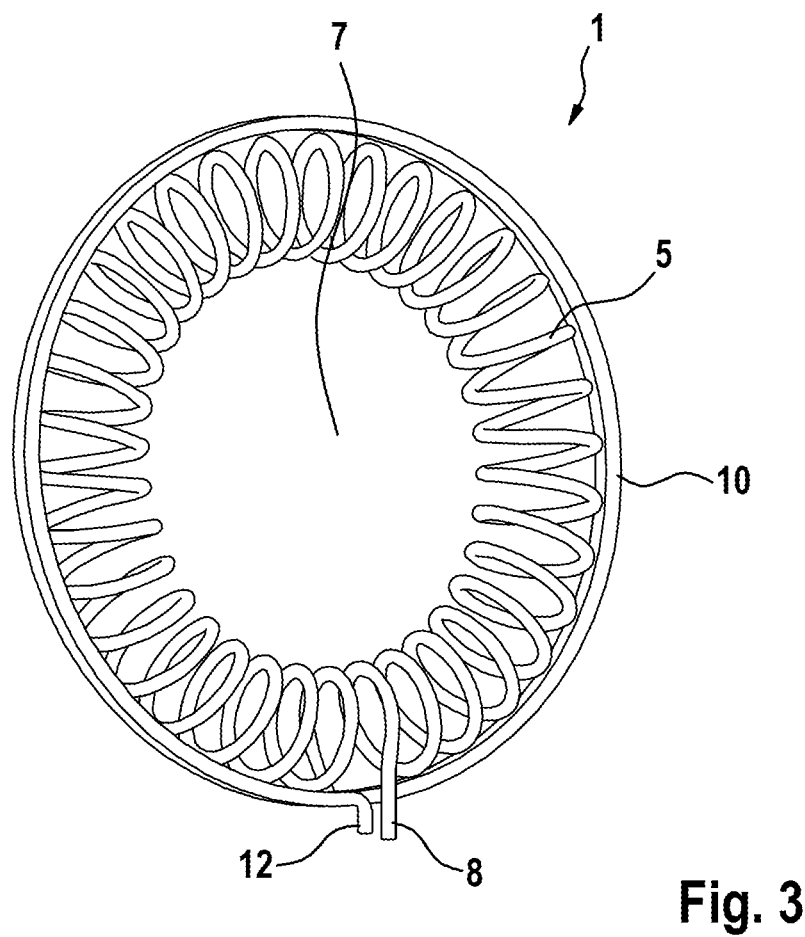

In the exemplary embodiment of the toroidal contact spring 1 illustrated in FIGS. 1-3, the ring 10 is formed as a double ring, which, in the region of the outer periphery of the toroidal coil 5, bears thereagainst and stabilizes the shape thereof. The ring 10 is thus connected at a number of points over its course to the toroidal coil 5 by means of, for example, laser welding or by self-curing electrically conductive plastics or adhesives. The second end 10.2 of the wire-shaped ring 10 forms the second connector pin 12. The first connector pin 8 and the second connector pin 12 protrude outwardly in the radial direction from the toroidal coil 5 or from the ring 10.

In the exemplary embodiment of a contact spring 1 illustrated in FIGS. 1-3, said contact spring is formed in one piece, that is to say the toroidal coil 5, the ring 10 and also the connector pins 8, 12 consist of a single piece of wire.

In accordance with the alternative possible embodiment, the coil 5, the ring 10 and also the connector pins 8, 12 are not formed in one piece, but are functionally identical to the aforementioned elements. In this case, the individual elements 5, 8, 10, 12 are suitably connected, in particular, are welded or soldered.

Figure 4:
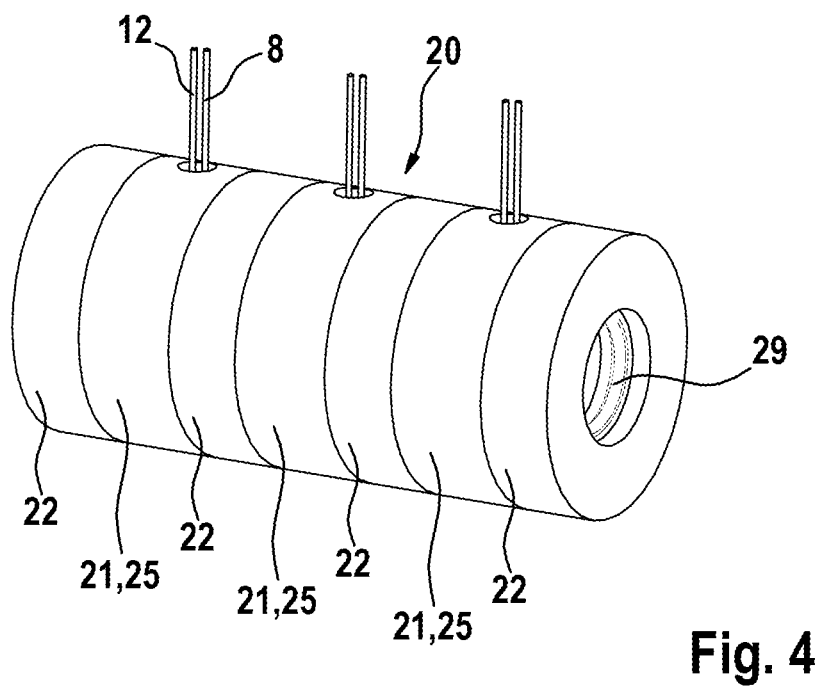
FIG. 4 shows a perspective view from the side of a plug contact socket of a terminal housing according to the present invention.
Figure 5:
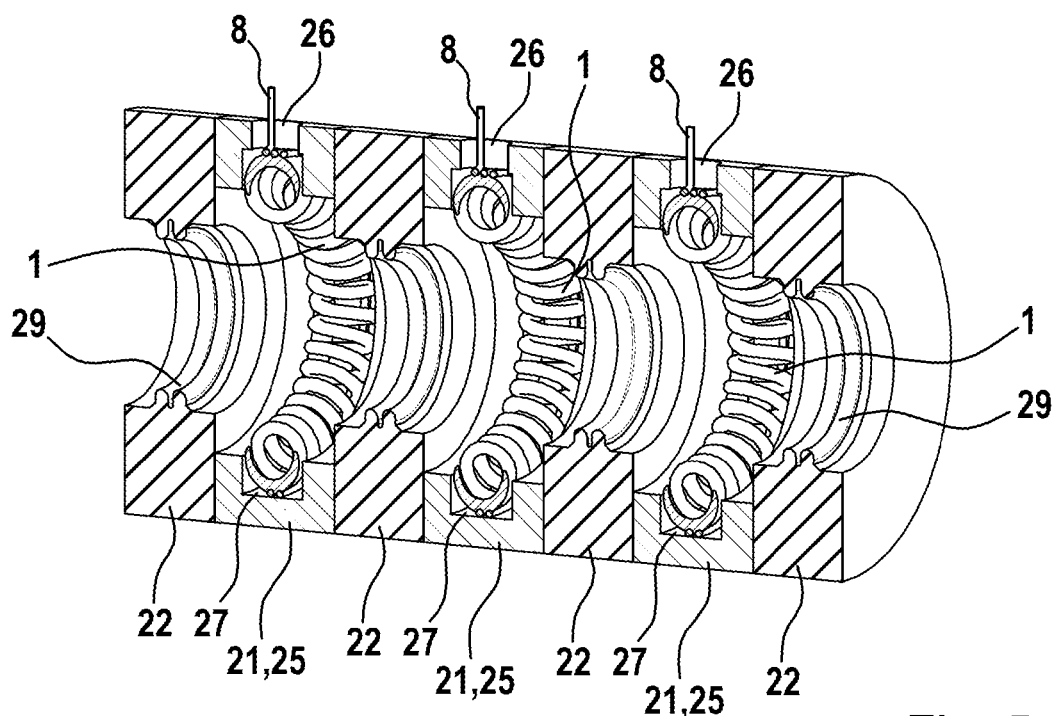
FIG. 5 shows a perspective view from the side of a cross-section of the plug contact socket according to FIG. 4.
Figure 6:
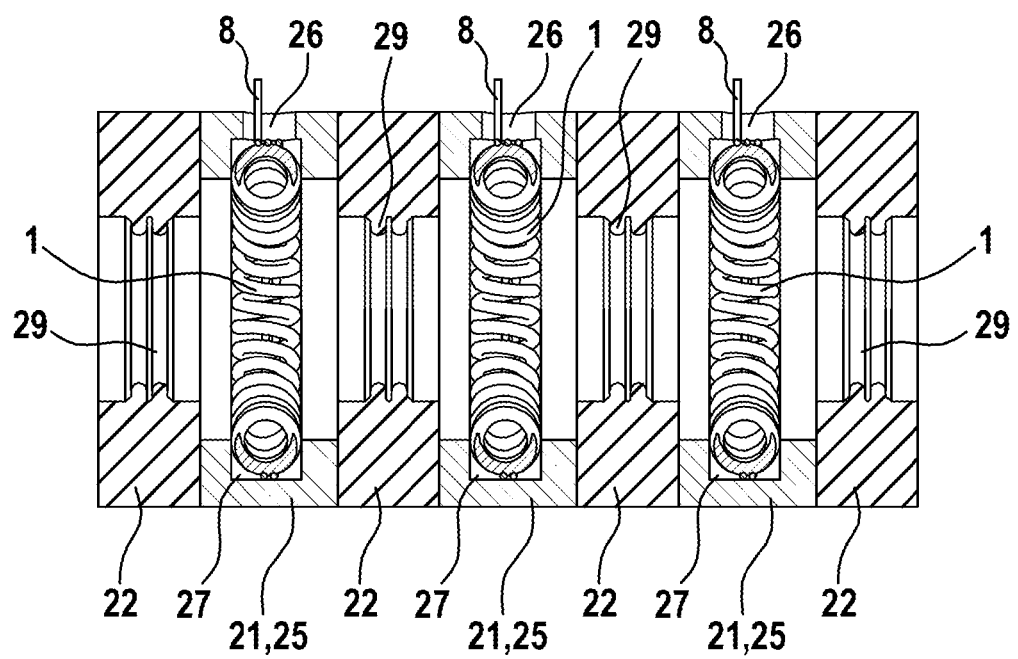
FIG. 6 shows a view from the front of the cross section according to FIG. 5.
Figure 7:
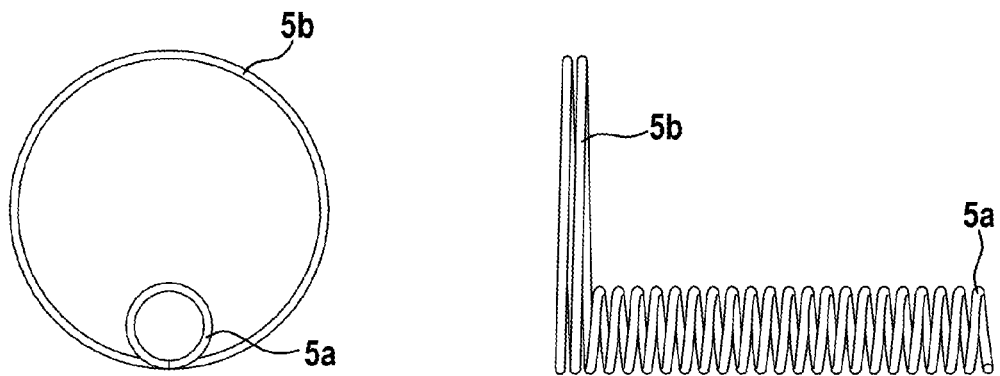
FIGS. 7-10 show the method according to the present invention for producing the spring contact component according to the present invention in the form of a toroidal contact spring according to FIGS. 1 to 3 in a number of steps.
Figure 8:
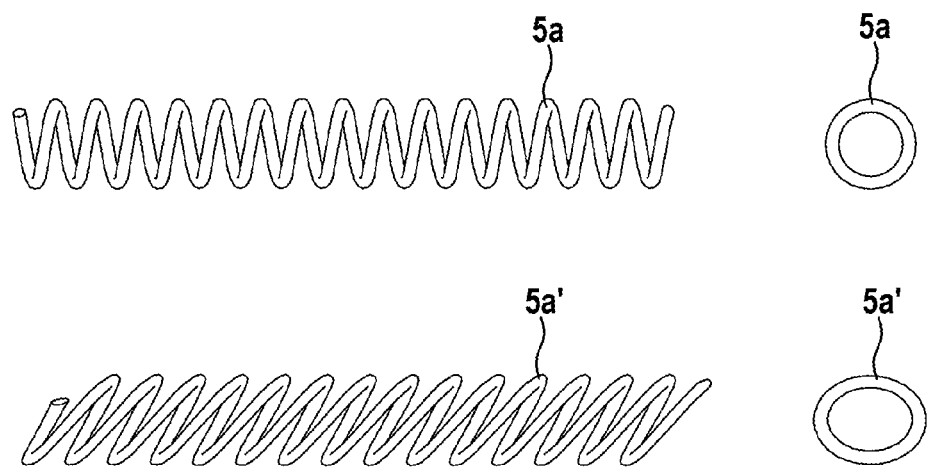

In FIGS. 4-6, a plug socket 20 of a header according to the present invention is illustrated and is assembled from three plug socket modules 21 and four sealing lip modules 22, alternately in each case.

In both alternative solutions, the housing of the contact socket component can consist of the same material or the same material group (for example, non-conductive polymers) as the sealing socket components. The housing of the contact socket component can thus also be fabricated from an electrically insulating material in the form of a cost-effective injection molded part. The electrically insulating material can be selected such that the different socket components can be glued together. A possible infiltration of liquid into the electrical contact region is thus advantageously prevented.

Each contact socket component 21 has a housing 25, for example, an annular or cylindrical housing, with a central continuous opening, an inner notch 27 arranged on the inner wall, and receiving the contact spring 1 illustrated in FIGS. 1-3. Each housing 25 is preferably fabricated as an injection molded part from silicone or other similar material. The opening 26, formed on the outer periphery of the housing 25 and continuous in the radial direction, serves as a bushing for the connector pins 8, 12 of the contact spring 1. This opening 26 is sealed around the protruding connector pins (wire ends) 8, 12, for example, by means of a silicone adhesive.

The sealing socket component 22 is likewise preferably produced as an injection molded part and comprises a cylindrical component with a central continuous opening. A sealing lip pair 29 is arranged on the inner opening wall.

A plug arranged in a plug contact socket 20 of this type can be considered to be floatingly mounted.

The production of the spring contact component 1 according to the present invention will now be described in the basis of FIGS. 7-10.

The spring contact component 1 consists of a single wire, which, for example, has a circular cross-section. This wire is initially shaped via a two-step winding process to produce two radial coils transitioning into one another, specifically a first coil 5a and a second coil 5b, having different diameters. The coils 5a, 5b are formed in this case as radial coils and have a uniform angle of inclination (see FIG. 7 with a view of the coils 5a, 5b from the side and a view from the front).

In a second step, the coil 5a having the smaller diameter is then deformed mechanically in a device, for example, in one or more rolls, such that a canted coil 5a' is produced from the radial coil 5a. The spring properties of the coil 5a' in the toroidal contact spring are predetermined by the degree of the canting (see FIG. 8 with a view of the coil 5a from the front and from the side before and after canting). In this case, the outer shape of the first coil 5a having the smaller diameter changes from circular (5a) to elliptical (5a').

Figure 9:
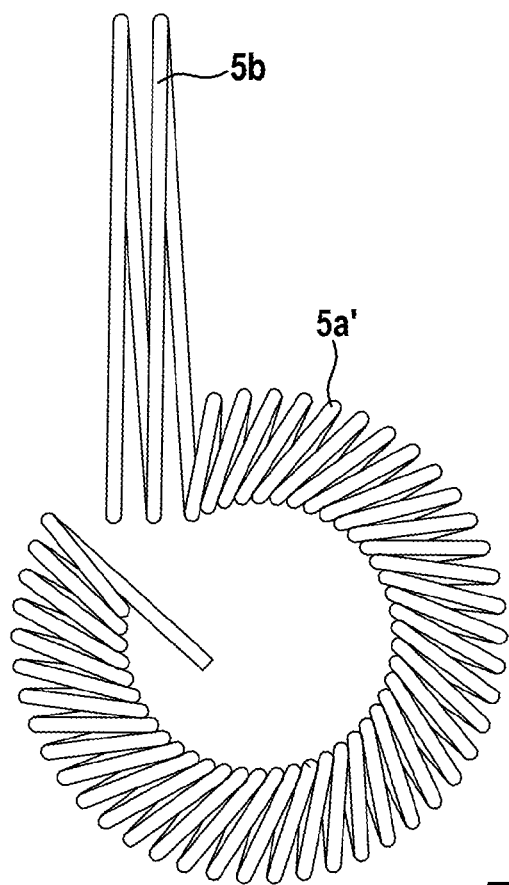
Figure 10:
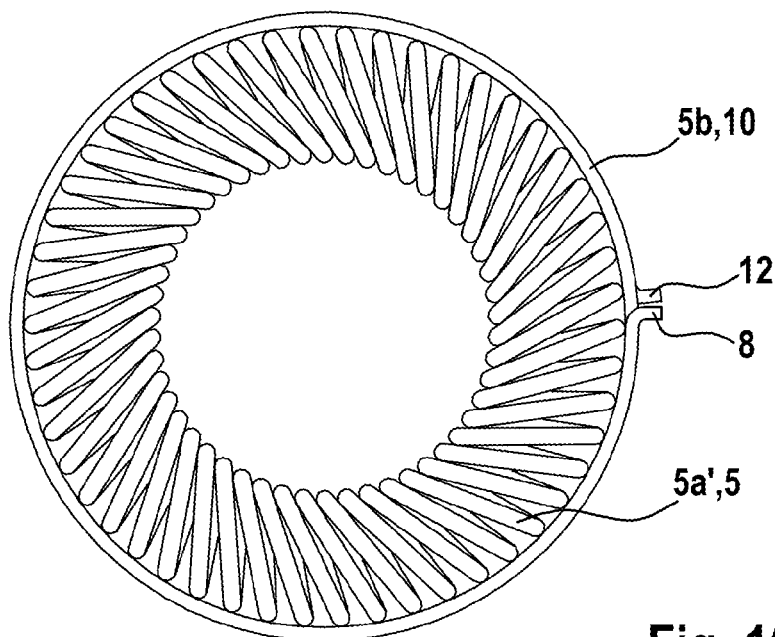

FIG. 9 shows the next step of the production method for the contact spring according to the present invention in a view from the side, in which the canted first coil 5a' is now brought mechanically into the shape of an open torus. The first coil 5a', which forms the open torus, is then rotated into the second coil 5b having the larger diameter, such that the first coil 5 in the illustration according to FIGS. 1 to 3 and the second coil 5b having the larger diameter forms the above-described peripheral ring 10 (see FIG. 10). As is illustrated in FIGS. 1-3, the ring 10 may have two windings, for example, that is to say it may be formed as a double ring 10. The ring 10 may alternatively, or also merely, have a single winding or more than two windings.

The peripheral ring 10 is then connected to the first coil 5a' or 5 by means of, for example, laser welding via a few laser welding spot welds or by self-curing electrically conductive plastics or adhesives. The first wire end 5.1 or the coil 5 and the second wire end 10.2 of the ring 10 each form a connector pin 8, 12, respectively, and are deformed (bent) in such a way that the connector pins 8, 12 protrude radially outwardly from the coil 5, the ring 10, or the contact spring 1. These connector pins 8, 12 are intended in a subsequent process step for electrically conductive attachment to the electronic elements provided in the housing of the implant.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

LIST OF REFERENCE SIGNS

1 spring contact component in the form of a toroidal contact spring with a peripheral coil
5 coil
5.1 first end of the coil 5
5.2 second end of the coil 5
5a, 5a' first coil
5b second coil
7 continuous contacting opening
8 connector pin
10 ring
10.1 first end of the ring 10
10.2 second end of the ring 10
12 connector pin
20 plug contact socket
21 contact socket component
22 sealing socket component
25 housing
26 opening
27 notch
29 sealing lip pair

We claim:

1. A spring contact component for a plug contact socket of an electromedical implant, the spring contact component comprising:
a coil surrounding an outer periphery of a plug opening, said coil having a first end and a second end, wherein the second end of the coil and a wire-shaped and/or strip-shaped element and also a connector pin are formed in one piece,
wherein the wire-shaped and/or strip-shaped element has a dimensionally stabilizing means surrounding the coil outwardly in the region of the periphery of said coil, said dimensionally stabilizing means being formed as a single or multiple ring or as a spiral.

2. The spring contact component as claimed in claim 1, wherein the dimensionally stabilizing means is connected at a number of points to the coil.

3. The spring contact component as claimed in claim 1, wherein the first end of the coil forms a connector pin.

4. A contact socket component for an electromedical implant comprising a spring contact component as claimed in claim 1.

5. The contact socket component as claimed in claim 4, wherein the spring contact component is inserted or embedded in a housing made of a non-conductive material and fabricated by means of injection molding, wherein a first connector pin and a second connector pin protrude from the housing in the region of the outer periphery.

6. A terminal housing for an electromedical implant comprising at least two contact socket components as claimed in claim 4 arranged side by side.

7. A spring contact component for a plug contact socket of an electromedical implant, the spring contact component comprising:
a coil surrounding an outer periphery of a plug opening, said coil having a first end and a second end, wherein the second end of the coil is electrically and mechanically connected directly to a connector pin via a wire-shaped and/or strip-shaped element, wherein the wire-shaped and/or strip-shaped element has a dimensionally stabilizing means surrounding the coil outwardly in the region of the periphery of said coil, said dimensionally stabilizing means being formed as a single or multiple ring or as a spiral.

8. The spring contact component as claimed in claim 7, wherein the coil and the wire-shaped and/or strip-shaped element are fabricated from the same electrically conductive material.

9. The spring contact component as claimed in claim 7, wherein the dimensionally stabilizing means is connected at a number of points to the coil.

10. The spring contact component as claimed in claim 7, wherein the first end of the coil forms a connector pin.

11. A method for producing a spring contact component for a plug contact socket of an electromedical implant with a coil surrounding the outer periphery of a continuous contacting opening, said method comprising the steps of:

producing a first coil and a second coil from a wire or a strip, wherein the first coil has a smaller diameter than the second coil;

forming an open torus from the first coil having the smaller diameter;

connecting, where appropriate, the first coil and the second coil together at one end of each coil; and screwing the first coil in the form of an open torus into the second coil in such a way that the second coil forms a single or multiple ring or spiral outwardly surrounding the first coil in the region of the periphery of said first coil.

12. The method as claimed in claim 11, wherein the first coil is canted before the torus is formed.

13. The method as claimed in claim 11, wherein the ring, once screwed in, is fastened at a number of points of the first coil, preferably by means of laser welding or by electrically conductive self-curing plastics or adhesives.

14. A spring contact component for a plug contact socket of an electromedical implant, the spring contact component comprising:

a coil surrounding an outer periphery of a plug opening, said coil having a first end and a second end, wherein the second end of the coil and a wire-shaped and/or strip-shaped element and also a connector pin are formed in one piece, wherein the coil is a torus spring and the wire-shaped and/or strip-shaped element is a single or multiple ring or a spiral outwardly surrounding the torus spring in the region of the periphery of said torus spring.

15. A spring contact component for a plug contact socket of an electromedical implant, the spring contact component comprising:

a coil surrounding an outer periphery of a plug opening, said coil having a first end and a second end, wherein the second end of the coil is electrically and mechanically connected directly to a connector pin via a wire-shaped and/or strip-shaped element, wherein the coil is a torus spring and the wire-shaped and/or strip-shaped element is a single or multiple ring or a spiral outwardly surrounding the torus spring in the region of the periphery of said torus spring.

* * * * *